United States Patent
Himmel et al.

(10) Patent No.: US 8,709,377 B2
(45) Date of Patent: Apr. 29, 2014

(54) MOLECULAR HYDROGEN STORES AND HYDROGEN TRANSFER REAGENTS FOR HYDROGENATION REACTIONS

(75) Inventors: Hans-Jörg Himmel, Sinsheim (DE); Elisabeth Kaifer, Heidelberg (DE); Oxana Ciobanu, Eppelheim (DE); Pascal Roquette, Heidelberg (DE); Walter Siebert, Dossenheim (DE)

(73) Assignee: Universitat Heidelberg, Heidelberg (DE)

( * ) Notice: Subject to any disclaimer, the term of this patent is extended or adjusted under 35 U.S.C. 154(b) by 1134 days.

(21) Appl. No.: 12/601,625

(22) PCT Filed: Apr. 15, 2008

(86) PCT No.: PCT/EP2008/003003
§ 371 (c)(1),
(2), (4) Date: Jan. 22, 2010

(87) PCT Pub. No.: WO2008/141705
PCT Pub. Date: Nov. 27, 2008

(65) Prior Publication Data
US 2010/0172825 A1 Jul. 8, 2010

(30) Foreign Application Priority Data
May 24, 2007 (DE) .......................... 10 2007 024 145

(51) Int. Cl.
| | | |
|---|---|---|
| *C01B 35/06* | (2006.01) | |
| *C01B 35/16* | (2006.01) | |
| *C01B 35/14* | (2006.01) | |
| *C01B 6/15* | (2006.01) | |
| *C07F 5/06* | (2006.01) | |

(52) U.S. Cl.
USPC ........... 423/644; 423/284; 423/286; 423/383; 564/9; 556/1; 556/175; 556/176; 556/178

(58) Field of Classification Search
USPC ............. 423/644, 284, 286, 383, 413, 648.1, 423/285; 564/9; 556/1, 175, 176, 178, 10
See application file for complete search history.

(56) References Cited

U.S. PATENT DOCUMENTS

2006/0292068 A1* 12/2006 Stephens et al. ........... 423/648.1

FOREIGN PATENT DOCUMENTS

EP 1475349 A2 11/2004

OTHER PUBLICATIONS

Marchant et al. "Synthesis and structural characterisation of primary amine adducts of gallane, RH2N•GaH3, and of their decomposition products, [RHNGaH2]n (R=Me, n=3; R=tBu, n=2)" Sep. 2005, The Royal Society of Chemistry Dalton Trans., p. 3281-3290.*
Himmel et al. "Heats of Hydrogenation of Compounds Featuring Main Group Elements and with the Potential for Multiply Bonding" 2002, Chem Eur. J, 8, No. 10 p. 2397-2405.*
Kohn, A. et al., "Why Does a Ga2 Dimer react Spontaneously with H2, but a Ga Atom Does Not?—A Detailed Quantum Chemical Investigation of the Differences in Reactivity Between Ga Atoms and Ga2 Dimers in Combination with Experimental Results", Chem, Eur. J. 2003,9,3909-3919.
Clark, T. et al., Transition-Metal-Catalyzed Dehydrocoupling: A Convenient Route to Bonds between Main-Group elements, Chem. Eur. J. 2006,12. 8634-8648.
Nie, Y. et al., "Halogen exchange at boron in nido-C4B2 Carboranes", Journal of Organometallic Chemistry 690 (2005), 4531-4536.
Stanger, A., "Stain-Induced Bond Localization. The Heteroatome Case", J. Am. Chem. Soc. 1998,120,12034-12040.
Robinson G. et al., A New Class of Binuclear Gallium Hydrides: Synthesis and Properties of [{GaCl(hpp)H}2] (hpp=1,3,4,6,7,8-Hexahydro-2H-pyrimido[1,2-a]pyrimidate), Chem. Eur. J. 2007, 13. 2648-2654.
International Search Report and Written Opinion from International Application No. PCT/EP2008/003003, filed Apr. 15, 2008, mailed on Nov. 30, 2009.

* cited by examiner

*Primary Examiner* — Wayne Langel
*Assistant Examiner* — Syed Iqbal
(74) *Attorney, Agent, or Firm* — Pergament Gilman & Cepeda LLP; Milagros A. Cepeda; Edward D. Pergament

(57) ABSTRACT

The present invention relates to a process for reversible hydrogen storage, to a material for reversible hydrogen storage and to the use of the material for reversible hydrogen storage.

11 Claims, No Drawings

MOLECULAR HYDROGEN STORES AND HYDROGEN TRANSFER REAGENTS FOR HYDROGENATION REACTIONS

The present invention relates to a process for reversible hydrogen storage, to a material for reversible hydrogen storage and to the use of the material for reversible hydrogen storage.

Hydrogen is an energy carrier which has great potential for future energy supply. For example, renewable energy can be stored directly in the form of hydrogen. In order to utilize this energy carrier effectively, however, suitable processes for hydrogen storage are needed. To date, the methods used for that purpose have been essentially (i) pressurized hydrogen gas storage, (ii) liquid hydrogen storage and (iii) metal hydride or hydride complex storage.

In pressurized hydrogen gas storage, storage pressures in the range from 20 to 30 MPa are typically used; however, there are now already storage tanks in the automotive sector which are designed for a pressure of about 70 MPa. To this end, storage tanks in a fiber composite design are generally used. The energy expenditure for the compression of the hydrogen gas to a pressure of 70 MPa is about 15% of the energy content of the hydrogen. The disadvantages of this method of hydrogen storage are, however, firstly the high pressures in the tanks and the associated risks, and secondly the self-ignitability of the hydrogen. For instance, a leak in a tank can result in serious accidents.

In the case of liquid hydrogen storage, hydrogen is liquefied at very low temperatures (in the region of 21 K). In this way, the pressure is not a problem for the configuration of the tank, and the reactivity of the hydrogen is also advantageously reduced after liquefaction. The disadvantage of this method of hydrogen storage lies, however, in the high energy needed for liquefaction. Thus, about 40% of the energy content of the hydrogen has to be expended for the liquefaction. Furthermore, the unavoidable evaporation losses of hydrogen in this process are also disadvantageous.

As an alternative to the aforementioned processes, it has been proposed to store hydrogen in the form of metal hydrides or hydride complexes. Such materials are in principle very suitable for storage of hydrogen. It is even possible in a metal hydride-based storage medium to achieve a higher density of hydrogen per cubic centimeter than in the case of liquefied hydrogen. The problem with this method of hydrogen storage lies, however, in the reversibility and the kinetics of the hydrogen desorption or absorption. U.S. Pat. No. 7,011,768 discloses, for example, the use of titanium-doped $NaAlH_4$ as a storage material for hydrogen. However, the kinetics of the hydrogen desorption and absorption in $NaAlH_4$/Ti are inadequate, which complicates effective utilization of this material as a hydrogen storage medium. DE 10 2006 013 457 A1, in contrast, describes the use of lanthanum-rich mixed metals for hydrogen storage. However, such mixed metals are comparatively expensive. Moreover, this type of materials requires the use of high pressures in order to store the hydrogen. WO 2006/060851 A1 describes a material for hydrogen storage based on magnesium-nickel with a refined eutectic structure. However, this material has the disadvantage that it is relatively expensive, and temperatures of more than 250° C. are needed for hydrogen storage. US 2007/0025908 A1 describes the use of $AlH_3$ as a material for hydrogen storage. However, reversibility is a problem in this type of storage materials. Moreover, hydrogen storage is unfavorable from a thermodynamic point of view, since $AlH_3$ is a comparatively stable solid. DE 601 24 677 T2 and US-A-2003/0052304 describe compositions which are capable of hydrogen absorption in a closed vessel at low pressure and comprise a substituted triazine and a hydrogenation catalyst. EP-A-1 475 349 and WO-A-2005/000457 describe the reversible hydrogenation of pi-conjugated substrates such as polycyclic aromatic hydrocarbons. WO-A-89/01823 describes an apparatus for dehydrogenating liquid hydrides, which comprises a chemical reactor for dehydrogenating the heated vaporous hydride, a preheating stage for preheating the hydride, an evaporator stage for evaporating the hydride, a superheating stage for superheating the vaporous hydride and a condenser stage for cooling the dehydrogenation products. US-A-2006/0292068 describes a process for dehydrogenating aminoboranes. JP-A-2003-277004 describes an apparatus for obtaining hydrogen gas from the reversible reaction of decalin to give naphthalene. A. Stanger, *J. Am. Chem. Soc.* 1998, 120, 12034 describes a theoretical study of the aromaticity, for example, of boron-containing aromatic molecules.

It is therefore an object of the present invention to provide a material for hydrogen storage, which has ideal reversibility and kinetics, and a sufficiently high percentage by mass of stored hydrogen, and entails comparatively low production costs, the use of such a material for reversible hydrogen storage and a process for reversible hydrogen storage.

This object is achieved by the embodiments characterized in the claims. More particularly, a process for reversible hydrogen storage is provided, which comprises the step of reacting a material for reversible hydrogen storage, comprising at least one compound of the general formula (III), (IV), (VI), (VII), (VIII) or (IX) below, with molecular hydrogen in order to reversibly store it, and/or heating it to a temperature in the range from 50° C. to 150° C. and/or placing a material which has reversibly stored hydrogen, comprising at least one compound of the general formula (I), (II), (III), (V), (VI), (VII) or (VIII) below, under vacuum in order to release molecular hydrogen:

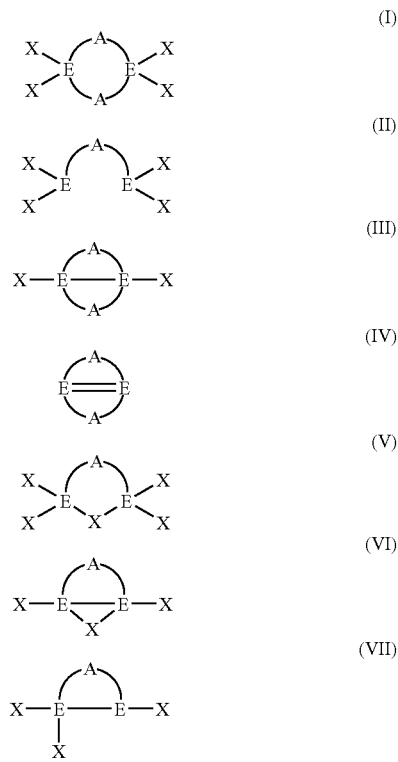

$$X-E\overset{\overset{A}{\frown}}{\text{———}}E-X \qquad \text{(VIII)}$$

$$E\overset{\overset{A}{\frown}}{=\!=\!=}E \qquad \text{(IX)}$$

where
E is selected from the group consisting of B, Al and Ga,
A is independently a $C_{1-8}$-alkylene group which may optionally be substituted by one or more $R^1$ radicals, a $C_{2-8}$-alkenylene group which may optionally be substituted by one or more $R^2$ radicals, an —$NR^3CR^4NR^5$— group, an —$NR^3$—$(CR^4R^4)_n$—$NR^5$— group where n=1-10 or an aromatic or heterocyclic ring which may optionally be substituted by one or more $R^6$ radicals,
$R^1$, $R^2$, $R^3$, $R^4$, $R^5$ and $R^6$ are each independently selected from hydrogen, halogen, hydroxyl, thio, cyano, sulfo, carboxyl, a straight- or branched-chain $C_{1-8}$-alkyl radical, a $C_{3-7}$-cycloalkyl radical, a straight- or branched-chain $C_{2-8}$-alkenyl radical, an aryl radical, a heterocyclic radical, an arylcarbonyl radical, a $C_{1-8}$-alkylcarbonyl radical, a carbonyloxy radical, a sulfonyl radical, an amino radical, a $C_{1-8}$-alkylamino radical, a $C_{1-8}$-dialkylamino radical, an amido radical, a $C_{1-8}$-alkylamido radical, a $C_{1-8}$-dialkylamido radical, a $C_{1-8}$-alkyloxycarbonylamino radical, an aryloxy-carbonylamino radical, an amidino radical, a guanidino radical, a $C_{1-8}$-alkyloxy radical, an aryloxy radical, an arylalkyloxy radical, a sulfonylamido radical, a $C_{1-8}$-alkylsulfonylamido radical, an arylsulfonylamido radical, an amino acid radical or a protected amino acid radical,
X is selected independently from hydrogen, halogen, hydroxyl, thio, cyano, sulfo, carboxyl, a straight- or branched-chain $C_{1-8}$-alkyl radical, a $C_{3-7}$-cycloalkyl radical, a straight- or branched-chain $C_{2-8}$-alkenyl radical, an aryl radical, a heterocyclic radical, an arylcarbonyl radical, a $C_{1-8}$-alkylcarbonyl radical, a carbonyloxy radical, a sulfonyl radical, an amino radical, a $C_{1-8}$-alkylamino radical, a $C_{1-8}$-dialkylamino radical, an amido radical, a $C_{1-8}$-alkylamido radical, a $C_{1-8}$-dialkylamido radical, a $C_{1-8}$-alkyloxycarbonylamino radical, an aryloxycarbonylamino radical, an amidino radical, a guanidino radical, a $C_{1-8}$-alkyloxy radical, an aryloxy radical, an arylalkyloxy radical, a sulfonylamido radical, a $C_{1-8}$-alkylsulfonylamido radical, an arylsulfonylamido radical, an amino acid radical or a protected amino acid radical,
where any two or more than two $R^1$ to $R^6$ and/or X radicals with one another may form one or more rings, and where the molecule may have two or more of the structural features shown in the formulae (I) to (IX), with the proviso that the compounds (I) to (IX) are capable either of absorbing and/or releasing hydrogen.

In the process according to the invention, it is firstly possible to rapidly and reversibly store hydrogen. This can be achieved by reacting at least one compound of the general formula (III), (IV), (VI), (VII), (VIII) or (IX) with molecular hydrogen. A prerequisite for such a hydrogen absorption is that the corresponding compounds of the general formula (III), (IV), (VI), (VII), (VIII) or (IX) are capable of storing hydrogen. In the context of the present invention, capability of storing hydrogen is understood to mean that the corresponding compound is at least monounsaturated with respect to an addition of hydrogen. Thus, these compounds contain at least one E-E bond which is split in the course of the addition of hydrogen according to the reaction of the following general type: E-E+$H_2$→2 E-H (E=B, Al or Ga).

The reaction of the compounds of the formula (III), (IV), (VI), (VII), (VIII) or (IX) with hydrogen affords compounds of the following general formula (I), (II), (III), (V), (VI), (VII) or (VIII) where at least two of the X substituents are hydrogen.

The reaction with hydrogen, i.e. hydrogenation, can be effected in any suitable manner. Corresponding processes for hydrogenation are known to those skilled in the art. The hydrogenation can be effected, for example, on the laboratory scale or on the industrial scale. In a preferred embodiment of the present invention, the hydrogenation is effected at a pressure in the range from about 0.1 to 5 bar, more preferably in the region of 1 bar. Such a hydrogenation is advantageous since no complex apparatus, for example an autoclave, need be used. This is particularly advantageous with regard to an industrial use of the process according to the invention, for example for reversible hydrogen storage in motor vehicle technology.

In the process according to the invention, it is likewise possible to release hydrogen in a rapid and reliable manner. To this end, the hydrogen-containing material which comprises at least one compound of the following general formulae (I), (II), (III), (V), (VI), (VII) or (VIII) is heated to a temperature in the range from 50 to 150° C., preferably in the range from 50 to 100° C., and/or placed under vacuum. Addition of a catalyst allows the temperature required for the elimination to be lowered and/or the formation of possible by-products to be suppressed. Suitable examples for this purpose are rhodium and titanium compounds such as chloro(1,5-cyclooctadiene)rhodium(I) dimer, and $Cp_2Ti$ ($Cp=C_5H_5$) prepared in situ from $Cl_2TiCp_2$/nBuLi, which lead to a lowering of the required temperature for the dehydrogenation of $H_3B(hppH)$ (hppH is the guanidine derivative 1,3,4,6,7,8-hexahydro-2H-pyrimido[1,2-a]pyrimidine) by about 20° C. In this way, the reaction of hydrogen absorption is reversed, which eliminates hydrogen from the compounds of the general formula (I), (II), (III), (V), (VI), (VII) or (VIII) and hence releases it in a controlled manner. A prerequisite for such a hydrogen release is that the corresponding compounds of the general formula (I), (II), (III), (V), (VI), (VII) or (VIII) are capable of releasing hydrogen. In the context of the present invention, capability of hydrogen release is understood to mean that the corresponding compound has at least one X substituent for which X is hydrogen. The corresponding compound preferably has at least two substituents for which X is hydrogen.

The heating can be effected in any suitable manner. The material can also be placed under vacuum in any suitable way. In the context of the present invention, the term "placing under vacuum" is understood to mean any reduction of the pressure. For example, in the context of the present invention, the pressure can be reduced to a value of about 100 mbar, even more preferred being a reduction of the pressure to a value of about 50 mbar, in order thus to bring about the release of hydrogen.

By the elimination of hydrogen, from a suitable aforementioned compound, it is surprisingly possible by means of the process according to the invention to release hydrogen in a controlled and safe manner when required. The hydrogen released in this way can be used in any suitable manner. For example, the hydrogen can be used to operate a fuel cell, for example in a motor vehicle, or for catalytic hydrogenation of olefins, both on the industrial scale and on the laboratory scale.

The process according to the invention is particularly advantageous because the hydrogen release and absorption can be very rapid. In a preferred embodiment of the present invention, the hydrogen release or absorption is essentially complete, i.e. to an extent of more than 95%, within less than 15 minutes, more preferably within less than 10 minutes and even more preferably within one minute.

The material used in the process according to the invention may be present either in liquid form or in the form of a molecular, oligomeric or polymeric solid. The state depends especially on the structure of the compounds of the general formulae (I) to (IX), i.e. especially on the nature of the A bridge and the X substituents, and on the way in which the compounds of the general formulae (I) to (IX) are processed within the material.

According to the present invention, E is selected from the group consisting of B, Al and Ga. In a preferred embodiment, all E atoms within the compound of one of the general formulae (I) to (IX) are identical and are the same element, B, Al or Ga. However, it is also possible that the compounds of the general formulae (I) to (IX) contain two different elements selected from the group consisting of B, Al and Ga. The use of these elements in the compounds of the general formulae (I) to (IX) for the process according to the invention for reversible hydrogen storage is particularly advantageous because the reaction of hydrogen absorption and the reverse reaction of hydrogen release are thus particularly favorable both in thermodynamic and in kinetic terms. For instance, the process according to the invention can be represented in simplified form by a reaction of the following general type: E-E+ $H_2 \rightarrow$ 2 E-H (E=B, Al or Ga), and the reverse reaction thereof. Since the electronegativity difference between E and H in this reaction is not too great, the reaction is only slightly exothermic or endothermic, and the free standard reaction enthalpy assumes a value at which the reaction can proceed in both directions under mild conditions from a purely thermodynamic point of view. In addition, a comparatively low reaction barrier is a further prerequisite for the reversibility of the reaction under mild conditions. In the process according to the invention, this prerequisite is also met, since it has been shown that the E-E and E-H bonds are not too strong when E=B, Al or Ga. Furthermore, in the process according to the invention, two E atoms are joined to one another via one or two bridging A ligands. In this way, the reaction barrier of the hydrogen absorption and release is reduced further, which brings about a further improvement in the reversibility of the reaction shown above. The process according to the invention for hydrogen release can thus be performed by using one or more elements selected from B, Al or Ga at comparatively low temperatures, specifically in the range from about 50° C. to about 150° C. Equally, the absorption of hydrogen can take place under very mild conditions.

The two E atoms are bridged to one another via at least one A bridge. The compounds of the general formulae (I), (III) and (IV) have two A bridges, where the A bridges may be the same or different. In the compounds of the general formulae (II), (V), (VI), (VII), (VIII) and (IX), one A bridge is present. A is a $C_{1-8}$-alkylene group which may optionally be substituted by one or more $R^1$ radicals, a $C_{2-8}$-alkenylene group which may optionally be substituted by one or more $R^2$ radicals, an —$NR^3CR^4NR^5$— group, an —$NR^3$—$(CR^4R^4)_n$—$NR^5$— group where n=1-10, or an aromatic or heterocyclic ring which may optionally be substituted by one or more $R^6$ radicals.

In the context of the present invention, a $C_{1-8}$-alkylene group is understood to mean a methylene, ethylene, propylene, butylene, pentylene, hexylene, heptylene or octylene group. The $C_{2-8}$-alkenylene group may be an ethenylene, propenylene, 1-butenylene, 2-butenylene, 1-pentenylene, 2-pentenylene or 1,3-pentadienylene group. In addition, the $C_{2-8}$-alkenylene group may also be any mono- or polyunsaturated hexenylene, heptenylene or octenylene group.

The A group may additionally be an —$NR^3CR^4NR^5$— group, this group being derived by hydrogen abstraction from an imine of the formula $NR^3$=$CR^4$—$NR^5H$ or $HNR^3$—$CR^4$=$NR^5$.

In addition, the A group may be an aromatic or heterocyclic ring, by means of which the two E atoms are joined to one another. Examples of appropriate aromatic groups are phenylene, naphthylene, phenanthrylene and anthracylene. The heterocyclic ring is a saturated or unsaturated, cyclic or polycyclic ring having, for example, 5 to 12 atoms, which contains one or more heteroatoms. Examples of appropriate heteroaromatic groups are thienediyl, furandiyl, pyrrolediyl, imidazolediyl, pyrazolediyl, thiazolediyl, isothiazolediyl, oxazolediyl, pyrrolidinediyl, pyrrolinediyl, imidazolidinediyl, imidazolinediyl, pyrazolidinediyl, tetrahydrofurandiyl, pyrandiyl, pyronediyl, pyridinediyl, pyrazinediyl, pyridazinediyl, benzofurandiyl, isobenzofurandiyl, indolediyl, oxyindolediyl, isoindolediyl, indazolediyl, indolinediyl, 7-azaindolediyl, isoindazolediyl, benzopyrandiyl, coumarindiyl, isocoumarindiyl, quinolediyl, isoquinolediyl, naphthridinediyl, quinnolinediyl, quinazolediyl, pyridopyridinediyl, benzoxazinediyl, quinoxadinediyl, chromenediyl, chromanediyl, isochromanediyl, carbolinediyl, oxadiazolediyl, thiadiazolediyl, triazolediyl, tetrazolediyl or pyrimidinediyl.

As explained above, the A groups may optionally be substituted by one or more $R^1$ to $R^6$ substituents, where the $R^1$ to $R^6$ substituents may be the same or different and it is also possible, for example, for a plurality of $R^1$ substituents to be different from one another. According to the present invention, the $R^1$ to $R^6$ substituents are each independently selected from hydrogen, halogen, hydroxyl, thio, cyano, sulfo, carboxyl, a straight- or branched-chain $C_{1-8}$-alkyl radical, a $C_{3-7}$-cycloalkyl radical, a straight- or branched-chain $C_{2-8}$-alkenyl radical, an aryl radical, a heterocyclic radical, an arylcarbonyl radical, a $C_{1-8}$-alkylcarbonyl radical, a carbonyloxy radical, a sulfonyl radical, an amino radical, a $C_{1-8}$-alkylamino radical, a $C_{1-8}$-dialkylamino radical, an amido radical, a $C_{1-8}$-alkylamido radical, a $C_{1-8}$-dialkylamido radical, a $C_{1-8}$-alkyloxy-carbonylamino radical, an aryloxy-carbonylamino radical, an amidino radical, a guanidino radical, a $C_{1-8}$-alkyloxy radical, an aryloxy radical, an arylalkyloxy radical, a sulfonylamido radical, a $C_{1-8}$-alkylsulfonylamido radical, an arylsulfonylamido radical, an amino acid radical or a protected amino acid radical.

The substituents designated halogen are understood to mean a halogen atom from the group of F, Cl, Br or I. Preferred halogen substituents are F, Cl and Br.

Examples of $C_{1-8}$-alkyl radicals are methyl, ethyl, isopropyl, n-propyl, isobutyl, tert-butyl, n-butyl, 1-, 2- or 3-pentyl, 2-methylbutyl, 3-methylbutyl, 1,1-dimethylpropyl, 1,2-dimethylpropyl, 2,2-dimethylpropyl, n-, 2- or 3-hexyl, 2-, 3- or 4-methylpentyl, 2-methyl-2-pentyl, 2,2-dimethylbutyl, 3,3-dimethylbutyl, 2,3-dimethylbutyl, 3-methyl-2-pentyl, 2-methyl-2-pentyl, 2,3-dimethyl-2-butyl and 3,3-dimethyl-2-butyl.

A $C_{3-7}$-cycloalkyl radical is understood to mean, for example, a cyclopropyl, a cyclobutane, a cyclopentane, a cyclohexane or a cycloheptane radical. Particular preference is given to a cyclohexane radical.

Examples of $C_{2-8}$-alkenyl radicals are an ethenyl, propenyl, 1-butenyl, 2-butenyl, 1-pentenyl, 2-pentenyl or 1,3-pentadienyl radical. In addition, the $C_{2-8}$-alkenyl group may also be any mono- or polyunsaturated hexenyl, heptenyl or octenyl group.

In the context of the present invention, an aryl radical is understood to mean a cyclic or polycyclic aromatic group, for example phenyl, naphthyl, phenanthryl and anthracyl. A heterocyclic radical is a saturated or unsaturated, cyclic or polycyclic radical which contains one or more heteroatoms. Examples of a heterocyclic radical are thienyl, furanyl, pyrrolyl, imidazolyl, pyrazolyl, thiazolyl, isothiazolyl, oxazolyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, benzofuranyl, isobenzofuryl, indolyl, oxyindolyl, isoindolyl, indazolyl, indolinyl, 7-azaindolyl, isoindazolyl, benzopyranyl, coumarinyl, isocoumarinyl, quinolyl, isoquinolyl, naphthridinyl, quinolinyl, quinazolinyl, pyridopyridyl, benzoxazinyl, quinoxadinyl, chromenyl, chromanyl, isochromanyl, carbolinyl, oxadiazolyl, thiadiazolyl, triazolyl, tetrazolyl or pyrimidinyl.

The aforementioned definitions for aryl and $C_{1-8}$-alkyl radicals apply correspondingly to other substituents which contain an aryl and/or $C_{1-8}$-alkyl group. These may be an arylcarbonyl radical, a $C_{1-8}$-alkylcarbonyl radical, a $C_{1-8}$-alkylamino radical, a $C_{1-8}$-dialkylamino radical, a $C_{1-8}$-alkylamido radical, a $C_{1-8}$-dialkylamido radical, a $C_{1-8}$-alkyloxycarbonylamino radical, an aryloxycarbonylamino radical, a $C_{1-8}$-alkyloxy radical, an aryloxy radical, an arylalkyloxy radical, a $C_{1-8}$-alkylsulfonylamido radical or an arylsulfonylamido radical.

In addition to the bridging A groups, the compounds of the general formulae (I) to (IX) according to the present invention may have X substituents which are bonded terminally to an E atom and/or connect two E atoms to one another in the manner of a bridge. The X substituents may be the same or different and may each independently be selected from hydrogen, halogen, hydroxyl, thio, cyano, sulfo, carboxyl, a straight- or branched-chain $C_{1-8}$-alkyl radical, a $C_{3-7}$-cycloalkyl radical, a straight- or branched-chain $C_{2-8}$-alkenyl radical, an aryl radical, a heterocyclic radical, an arylcarbonyl radical, a $C_{1-8}$-alkylcarbonyl radical, a carbonyloxy radical, a sulfonyl radical, an amino radical, a $C_{1-8}$-alkylamino radical, a $C_{1-8}$-dialkylamino radical, an amido radical, a $C_{1-8}$-alkylamido radical, a $C_{1-8}$-dialkylamido radical, a $C_{1-8}$-alkyloxycarbonylamino radical, an aryloxycarbonylamino radical, an amidino radical, a guanidino radical, a $C_{1-8}$-alkyloxy radical, an aryloxy radical, an arylalkyloxy radical, a sulfonylamido radical, a $C_{1-8}$-alkylsulfonylamido radical, an arylsulfonylamido radical, an amino acid radical or a protected amino acid radical. The particular definitions correspond to those for the $R^1$ to $R^6$ substituents.

In a preferred embodiment of the present invention, the X substituents are each independently hydrogen, halogen, especially fluorine, an amino radical, a $C_{1-8}$-alkylamino radical or a $C_{1-8}$-dialkylamino radical. For stabilization reasons, this is particularly advantageous with regard to hydrogen absorption or release.

According to the present invention, the compounds (I) to (IX) are capable either of absorbing and/or of releasing hydrogen. In the context of the present invention, the ability to release hydrogen is understood to mean that the corresponding compound has at least one X substituent for which X is hydrogen. The corresponding compound preferably contains at least two substituents for which X is hydrogen. This relates exclusively to the compounds of the general formulae (I), (II), (III), (V), (VI), (VII) and (VIII), since these have X substituents. Moreover, in the context of the present invention, the ability to absorb hydrogen is understood to mean that the corresponding compound is at least monounsaturated with regard to an addition of hydrogen. These compounds contain at least one E-E bond which is split in the course of the addition of hydrogen by the reaction of the following general type E-E+$H_2$→2 E-H (E=B, Al or Ga). This relates exclusively to the compounds of the general formulae (III), (IV), (VI), (VII), (VIII) and (IX). It is evident from the above that the present invention also relates to compounds which are capable both of hydrogen absorption and of hydrogen release. These are the compounds of the general formulae (III), (VI), (VII) and (VIII).

It is additionally possible that any two or more than two $R^1$ to $R^6$ and/or X radicals form one or more rings with one another and/or that the molecule has two or more of the structural features shown in the formulae (I) to (IX).

In a preferred embodiment of the present invention, A is an —$NR^3CR^4NR^5$— group and X is hydrogen, halogen, a straight- or branched-chain $C_{1-8}$-alkyl radical or $NH_2$. The A group is preferably an amidinate with $R^4$ as hydrogen or $C_{1-8}$-alkyl radical, or a guanidinate with $R^4$ as $C_{1-8}$-dialkylamino radical. The use of amidinate bridges is advantageous with regard to the storage capacity of hydrogen. For instance, when amidinate bridges are used, up to about 6% by weight of hydrogen can be stored in the compounds of the general formula (I). Amidinate and guanidinate bridges are also advantageous from a kinetic and thermodynamic point of view. For instance, it has been calculated that, for a compound of the general formula (I) where E=B, A=—$NR^3CR^4NR^5$— and $R^3$, $R^4$, $R^5$ and X=hydrogen, the release of hydrogen is only slightly endothermic at +50 kJ/mol and this reaction has a free reaction enthalpy ($\Delta G°$) of +28 kJ/mol (1 bar, 25° C.). For the corresponding compound where E=Ga, the hydrogen release is slightly exothermic at −20 kJ/mol and the free reaction enthalpy ($\Delta G°$) is −44 kJ/mol (1 bar, 25° C.). When a guanidinate bridge is used instead of an amidinate bridge, it is found that, for the compound of the general formula (I) where E=B, A=—$NR^3CR^4NR^5$—, $R^3$, $R^5$ and X=hydrogen, and $R^4$=$NH_2$, the hydrogen release is endothermic at +46 kJ/mol and this reaction has a free reaction enthalpy ($\Delta G°$) of +19 kJ/mol (1 bar, 25° C.). For the corresponding compound where E=Ga, the hydrogen release is slightly exothermic at −7 kJ/mol and the free reaction enthalpy ($\Delta G°$) is −33 kJ/mol (1 bar, 25° C.).

Especially preferably, A is therefore one of the following groups (X) to (XII):

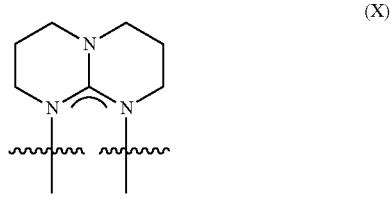

(X)

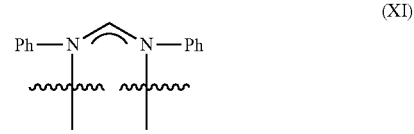

(XI)

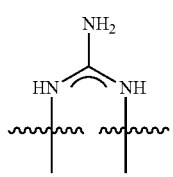

where the (X) to (XII) radicals may be substituted by one or more straight- or branched-chain $C_{1-8}$-alkyl radicals, aryl radicals and/or halogen atoms.

In a particularly preferred embodiment of the present invention, the material used in the process according to the invention comprises at least one compound of the following formulae (XIII) to (XV):

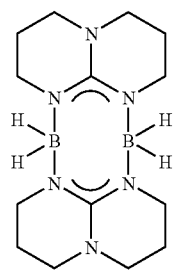

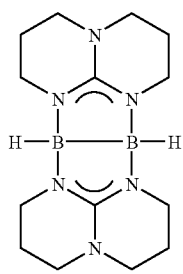

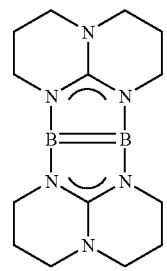

In another preferred embodiment of the present invention, A is a $C_2$-alkenylene group which may be substituted by one or more $C_{1-8}$-alkyl radicals, aryl radicals and/or halogen atoms, and X is hydrogen, halogen, a straight- or branched-chain $C_{1-8}$-alkyl radical or $NH_2$.

In a particularly preferred embodiment of the present invention, the material used in the process according to the invention comprises at least one compound of the following formula (XVI):

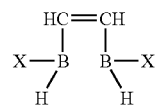

The compound of the formula (XVI) is especially advantageous with regard to the hydrogen storage capacity. For instance, the compound can eliminate up to about 8% by weight of hydrogen to form a corresponding diboracyclobutene derivative.

In a further preferred embodiment of the present invention, the A radical is an aromatic ring which may be substituted by one or more $C_{1-8}$-alkyl radicals, aryl radicals and/or halogen atoms, and X is hydrogen, halogen, a straight- or branched-chain $C_{1-8}$-alkyl radical or $NH_2$. In a particularly preferred embodiment of the present invention, the material used in the process according to the invention comprises at least one compound of the following formula (XVII), where X is halogen or hydrogen:

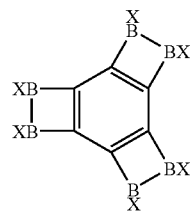

In a further preferred embodiment of the present invention, the material used in the process according to the invention comprises at least one compound of the following formula (XVIII):

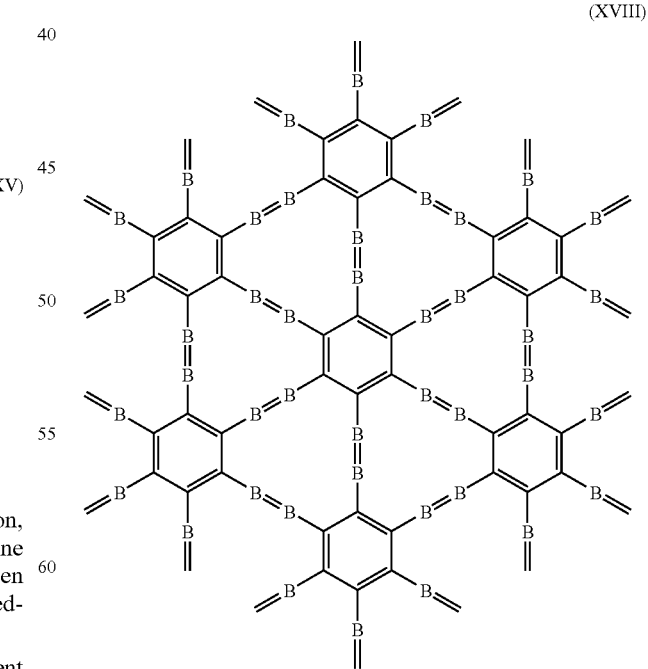

The process according to the invention surprisingly enables rapid and reversible hydrogen storage at a comparatively low pressure. The pressure is preferably in the range from about 0.1 to 5 bar, more preferably a pressure of about 1 bar. In addition, the process according to the invention can be performed at comparatively mild temperatures of less than 150° C. The high flexibility with regard to the selection of the bridging A ligand and of the X substituent is also advantageous with regard to an adjustment of the process according to the invention to different applications, for example hydrogen storage in the context of motor vehicle technology or hydrogen release in stoichiometric olefin hydrogenation. In addition, the material used in the process according to the invention is comparatively simple and inexpensive to produce.

The present invention further relates to a material for reversible hydrogen storage, comprising at least one compound of the following general formulae (I) to (IX), where E is boron and the A and X groups are each as defined above:

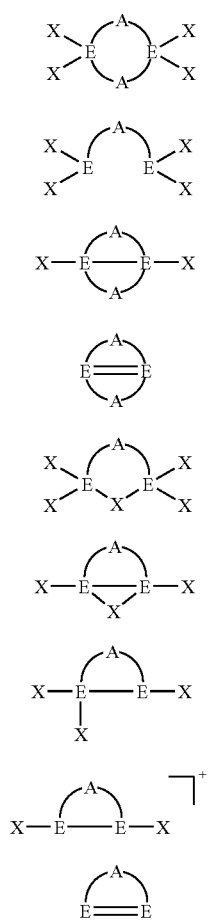

According to the present invention, the compounds (I) to (IX) are capable either of absorbing and/or of releasing hydrogen. In the context of the present invention, the ability to release hydrogen is understood to mean that the corresponding compound has at least one X substituent for which X is hydrogen. The corresponding compound preferably contains at least two substituents for which X is hydrogen. This relates exclusively to the compounds of the general formulae (I), (II), (III), (V), (VI), (VII) and (VIII), since these have X substituents. Moreover, in the context of the present invention, the ability to absorb hydrogen is understood to mean that the corresponding compound is at least monounsaturated with regard to an addition of hydrogen. These compounds contain at least one E-E bond which is split in the course of the addition of hydrogen by the reaction of the following general type E-E+$H_2$→2 E-H (E=B). This relates exclusively to the compounds of the general formulae (III), (IV), (VI), (VII), (VIII) and (IX). It is evident from the above that the present invention also relates to compounds which are capable both of hydrogen absorption and of hydrogen release. These are the compounds of the general formulae (III), (VI), (VII) and (VIII).

It is thus possible with the inventive material to rapidly and reversibly store hydrogen and/or to rapidly and safely release hydrogen. In a preferred embodiment of the present invention, the hydrogen release or absorption is essentially complete, i.e. to an extent of more than 95%, within less than 15 minutes, more preferably within less than 10 minutes and even more preferably within one minute.

The inventive material may be present either in liquid form or in the form of a molecular, oligomeric or polymeric solid. The state depends more particularly on the structure of the compounds of the general formulae (I) to (IX), i.e. more particularly on the nature of the A bridge and of the X substituents, and on the way in which the compounds of the general formulae (I) to (IX) are processed within the material.

In a preferred embodiment of the present invention, A is an —$NR^3CR^4NR^5$— group and X is hydrogen, halogen, a straight- or branched-chain $C_{1-8}$-alkyl radical or $NH_2$. A is especially preferably one of the following groups (X) to (XII):

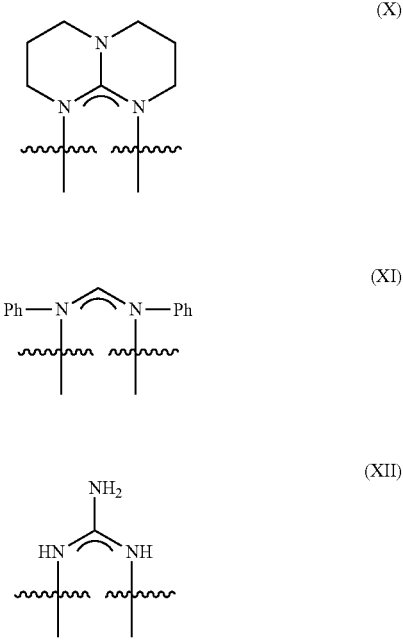

where the (X) to (XII) radicals may be substituted by one or more straight- or branched-chain $C_{1-8}$-alkyl radicals, aryl radicals and/or halogen atoms.

In a particularly preferred embodiment of the present invention, the inventive material comprises at least one compound of the following formulae (XIII) to (XV)

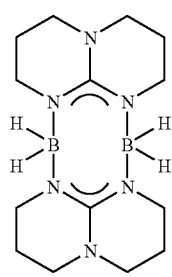
(XIII)

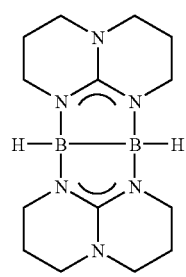
(XIV)

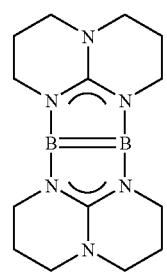
(XV)

In another preferred embodiment of the present invention, A is a $C_2$-alkenylene group which may be substituted by one or more $C_{1-8}$-alkyl radicals, aryl radicals and/or halogen atoms, and X is hydrogen, halogen, a straight- or branched-chain $C_{1-8}$-alkyl radical or $NH_2$.

In a particularly preferred embodiment of the present invention, the inventive material comprises at least one compound of the following formula (XVI):

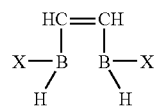
(XVI)

In a further preferred embodiment of the present invention, the A radical is an aromatic ring which may be substituted by one or more $C_{1-8}$-alkyl radicals, aryl radicals and/or halogen atoms, and X is hydrogen, halogen, a straight- or branched-chain $C_{1-8}$-alkyl radical or $NH_2$. In a particularly preferred embodiment of the present invention, the inventive material comprises at least one compound of the following formula (XVII) where X is halogen or hydrogen.

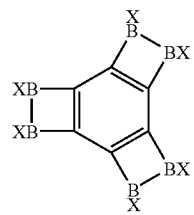
(XVII)

In a further preferred embodiment of the present invention, the inventive material comprises at least one compound of the following formula (XVIII):

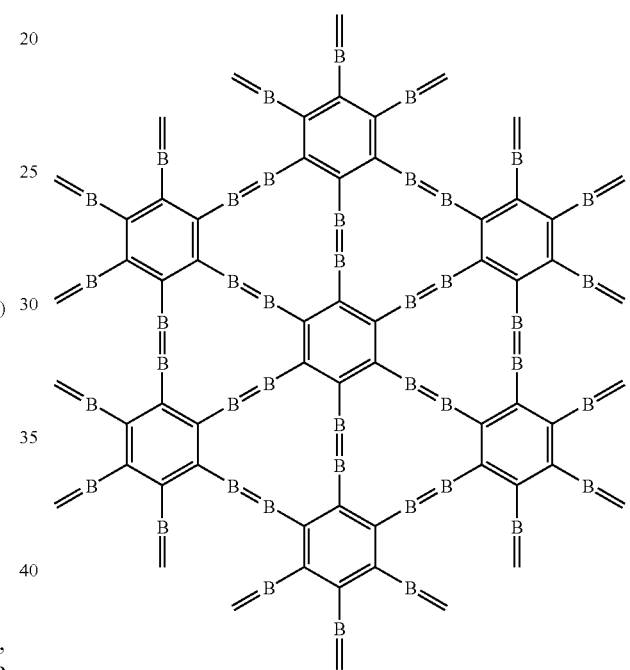
(XVIII)

The present invention further relates to the use of the material shown above for reversible hydrogen storage. In the context of the present invention, reversible hydrogen storage is understood to mean a process which comprises firstly the reaction of the inventive material with hydrogen for hydrogen absorption and secondly the release of hydrogen from the hydrogen-containing material obtained by hydrogen absorption. The inventive material can be used, for example, as a hydrogen store in fuel cell technology, for example in the motor vehicle sector, or else for release of hydrogen for olefin hydrogenation either on the laboratory scale or on the industrial scale.

The compounds of the general formulae (I) to (IX) can be prepared in any suitable manner. Corresponding processes are known to those skilled in the art.

For example, the compound of the general formula (III) (E=B) can be obtained by the reaction shown in the following reaction scheme (1):

Reaction scheme (1)

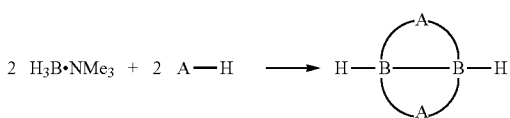

The compound obtained in this reaction is able to reversibly absorb and release hydrogen according to the following reaction scheme (2):

Reaction scheme (2)

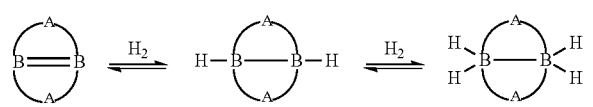

In addition, the inventive compounds can be prepared with only one A bridge, for example, in the following manner (reaction scheme (3) and reaction scheme (4)), where E is boron and Y is a halogen, preferably chlorine:

Reaction scheme (3)

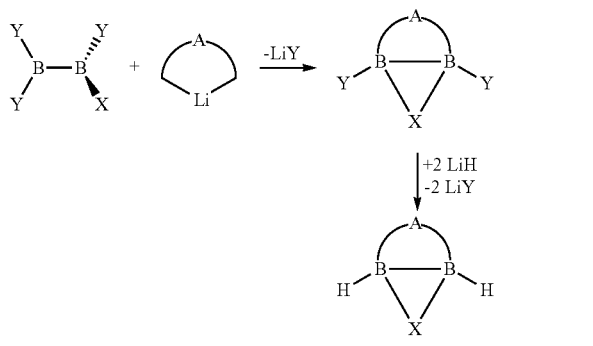

Reaction scheme (4)

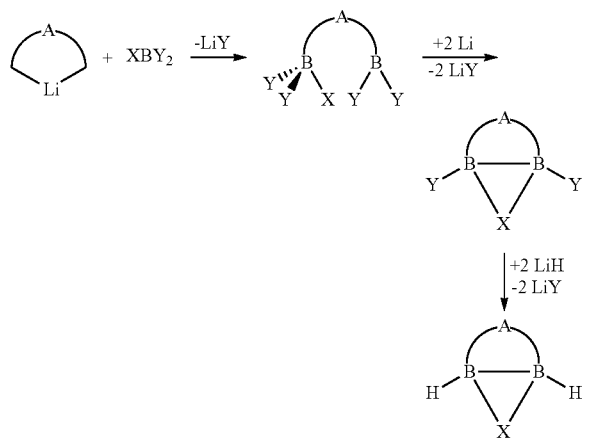

The structure of the inventive compounds obtained may be of the salt (general formula (VIII)) or covalent (general formulae (VI) and (VII)) type. This depends essentially on the nature (electronic and steric properties) of the X substituent.

When the compound obtained is of the salt type (general formula (VIII)), the counteranion may be any desired suitable anion. It is preferably, however, identical to the X substituent. The counterion is more preferably a halide.

Reaction scheme (5) below shows how, proceeding from a diborylated alkyne derivative, obtainable by reaction of $CaC_2$ with $BX_3$—$OEt_2$, catalytic cyclotrimerization can form a hexaborylbenzene derivative. Reduction with Li or another suitable reducing agent gives rise to the compound of the general formula (XVII) according to the present invention.

Reaction scheme (5)

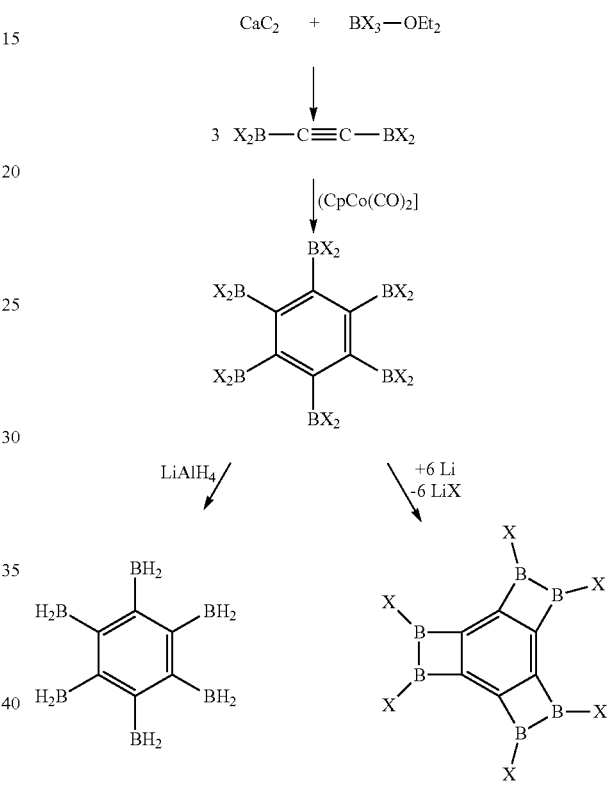

When $X_2$ elimination is possible (for example when X is hydrogen) in the compound of the general formula (XVII), $X_2$ elimination can form the oligomer or polymer of the general formula (XVIII).

The present invention is illustrated in detail by way of example hereinafter, but without being restricted thereto.

EXAMPLE

Synthesis of the diborodiguanidinatodihydride [HB(hpp)]$_2$

To a solution of $H_3B \cdot NMe_3$ (0.21 g, 2.9 mmol) in 15 ml of toluene is slowly added a solution of hppH (1,3,4,6,7,8-hexahydro-2H-pyrimido[1,2-a]pyrimidine, 0.4 g, 2.9 mmol) in 15 ml of toluene, and then the mixture is heated to boiling under reflux at 115° C. for 20 h. Thereafter, the solution which has been cooled to room temperature is concentrated and the [HB(hpp)]$_2$ product is crystallized at −20° C. in a yield of 70%. $^1$H NMR (600 MHz, $C_6D_6$): δ=3.23 (t, 1H, $^3J$=5.8 Hz, $C^1H_2$), 2.57 (t, 1H, $^3J$=6.6 Hz, $C^3H_2$), 1.56 (quin, 1H, $C^2H_2$). $^{13}$C{$^1$H}NmR (150.9 MHz, $C_6D_6$): δ=47.96 ($C^3$), 47.19 ($C^1$), 24.21 ($C^2$). $^{11}$B{$^1$H}NMR (192.5 MHz, $C_6D_6$): δ=−2.39

(BH). MS (EI⁺, m/z): 299.4 [$C_{14}H_{26}B_2N_6^+$], 138.2 [hpp⁺]. IR(CsI(s), cm⁻¹): 2964 m (C—H), 2852 m (C—H), 2398-2230 m (B—H), 1565 s (C—N), 1321 m (B—N).

In an alternative reaction sequence, it is first possible, in a first step, to prepare the precursor molecule $H_3B.hppH$, by slowly adding, to a solution of hppH (1.00 g, 7.18 mmol) in 20 ml of toluene, a solution of $H_3B.NMe_3$ (0.524 g, 7.18 mmol) in 20 ml of toluene, and stirring the reaction solution at 60° C. for 18 h. Subsequently, the reaction mixture is concentrated, and addition of pentane precipitates the $H_3B.hppH$ precursor molecule as a colorless precipitate in a yield of 70%. Anal. calculated (153.03): calculated: C, 54.94; H, 10.54; N, 27.46. found: C, 54.36; H, 10.38; N, 26.91. ¹H NMR (400 MHz, $C_6D_6$): δ=6.29 (s, 1H, NH), 3.34 (t, 2H, ³J=5.9 Hz, $C^8H_2$), 2.83 (br q, 3H, ¹J=93 Hz, $BH_3$), 2.27 (t, 2H, ³J=5.9 Hz, $C^6H_2$), 2.13 (t, 2H, ³J=6.0 Hz, $C^{10}H_2$), 2.03 (t, 2H, ³J=6.0 Hz, $C^2H_2$), 1.17 (quin, 2H, ³J=6.0 Hz, $C^9H_2$), 0.91 (quin, 2H, ³J=6.0 Hz, $C^1H_2$). ¹³C NMR{¹H}(100.55 MHz, $C_6D_6$): δ=150.69 ($C^4$), 47.47 ($C^8$), 47.27 ($C^{10}$), 46.82 ($C^2$), 38.38 ($C^6$), 21.80 ($C^9$), 21.57 ($C^1$). ¹¹B NMR (128.30 MHz, $C_6D_6$): δ=−19.15 (q, ¹J=93 Hz, $BH_3$). Mass Spec. (HR-EI⁺, m/z): 152.14 ([M-H]⁺, 100.0%), 138.10 ([hpp]⁺, 28.2%), 122.09 ([M-$CH_3NH_2$]⁺, 5.6%), 113.00 ([M-$CH_3NB$]⁺, 5.1%), 95.07 ([M-$C_2H_9NB$]⁺, 2.8%). IR(CsI(s), cm⁻¹): 3352 s (N—H val.), 2960 m (C—H val.), 2872 m (C—H val.), 2363 m (B—H), 2301 m (B—H), 2253 m (B—H), 1625 s (C=N val.), 1570 s (N—H def.), 1447 w (C—H def.), 1322 m, 1174 m (B—N), 1148 m.

Heating the precursor molecule $H_3B.hppH$ to a temperature of 115° C. quantitatively forms the hydrogen store [HB(hpp)]$_2$ with release of $H_2$.

The invention claimed is:

1. A process for reversible hydrogen storage, comprising the reaction of a material for reversible hydrogen storage, comprising at least one compound of the general formula (III), (IV), (VI), (VII), (VIII) or (IX) below, with molecular hydrogen in order to reversibly store it, and/or heating it to a temperature in the range from 50° C. to 150° C. and/or placing a material which has reversibly stored hydrogen, comprising at least one compound of the general formula (I), (II), (III), (V), (VI), (VII) or (VIII) below, under vacuum in order to release molecular hydrogen:

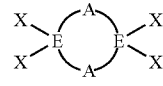
(I)

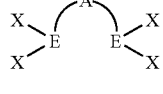
(II)

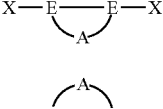
(III)

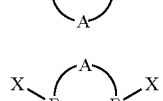
(IV)

(V)

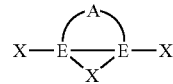
(VI)

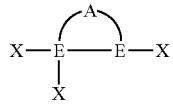
(VII)

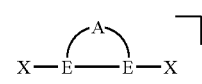
(VIII)

(IX)

where
E is selected from the group consisting of B, Al and Ga,
A is one of the following groups (X) to (XII):

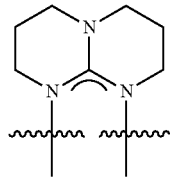
(X)

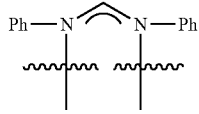
(XI)

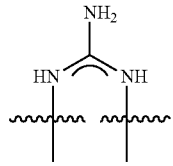
(XII)

where the (X) to (XII) radicals may be substituted by one or more straight- or branched-chain $C_{1-8}$-alkyl radicals aryl radicals and/or halogen atoms, X is from hydrogen, halogen, hydroxyl, thio, cyano, sulfo, carboxyl, a straight- or branched-chain $C_{1-8}$-alkyl radical, a $C_{3-7}$-cycloalkyl radical, a straight- or branched-chain $C_{2-8}$-alkenyl radical, an aryl radical, a heterocyclic radical, an arylcarbonyl radical, a $C_{1-8}$-alkylcarbonyl radical, a carbonyloxy radical, a sulfonyl radical, an amino radical, a $C_{1-8}$-alkylamino radical, a $C_{1-8}$-dialkylamino radical, an amido radical, a $C_{1-8}$-alkylamido radical, a $C_{1-8}$-dialkylamido radical, a $C_{1-8}$-alkyloxycarbonylamino radical, an aryloxycarbonylamino radical, an amidino radical, a guanidino radical, a $C_{1-8}$-alkyloxy radical, an aryloxy radical, an arylalkyloxy radical, a sulfonylamido radical, a $C_{1-8}$-alkylsulfonylamido radical, an arylsulfonyl-amido radical, an amino acid radical or a protected acid radical, where the molecule may have two or more of the structural features shown in the formulae (I) to (IX), with the proviso that the compounds (I) to (IX) are capable either of absorbing and/or releasing hydrogen.

2. The process as claimed in claim 1, wherein the material comprises at least one compound of the following formulae (XIII) to (XV):

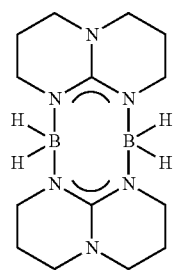

(XIII)

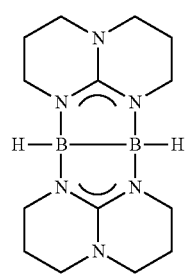

(XIV)

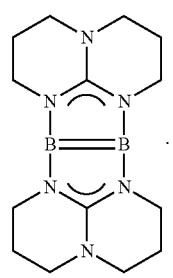

(XV)

3. A process for reversible hydrogen storage, comprising the reaction of a material for reversible hydrogen storage, comprising at least one compound of the general formula (XVI) below, with molecular hydrogen in order to reversibly store it, and/or heating it to a temperature in the range from 50° C. to 150° C. and/or placing the material which has reversibly stored hydrogen, comprising at least one compound of the general formula (XVI) below, under vacuum in order to release molecular hydrogen:

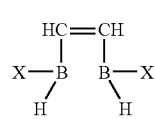

(XVI)

wherein X is as defined in claim 1.

4. A process for reversible hydrogen storage, comprising the reaction of a material for reversible hydrogen storage comprising at least one compound of the general formula (XVII) below, with molecular hydrogen in order to reversibly store it, and/or heating it to a temperature in the range from 50° C. to 150° C. and/or placing the material which has reversibly stored hydrogen, comprising at least one compound of the general formula (XVI) below, under vacuum in order to release molecular hydrogen:

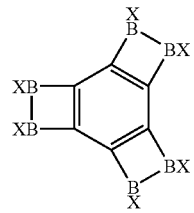

(XVII)

where X is halogen or hydrogen.

5. A process for reversible hydrogen storage, comprising the reaction of a material for reversible hydrogen storage, comprising at least one compound of the general formula (XVIII) below, with molecular hydrogen in order to reversibly store it, and/or heating it to a temperature in the range from 50° C. to 150° C. and/or placing the material which has reversibly stored hydrogen, comprising at least one compound of the general formula (XVIII) below, under vacuum in order to release molecular hydrogen:

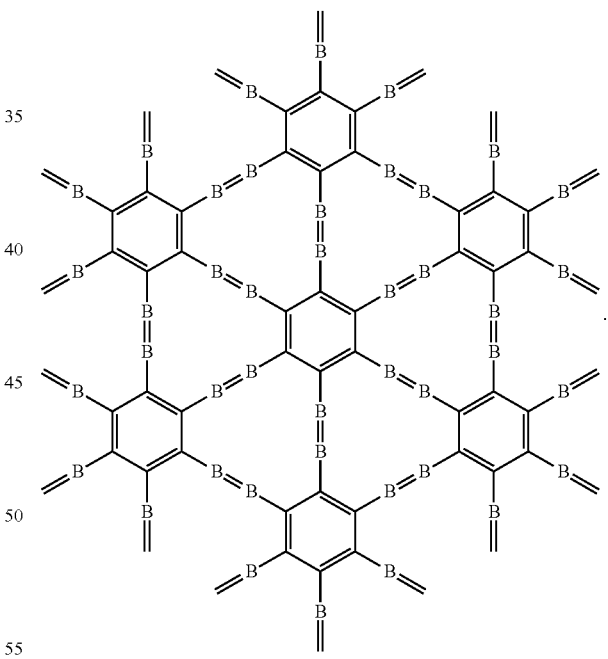

(XVIII)

6. A material for reversible hydrogen storage, comprising at least one compound of the following general formulae (I) to (IX):

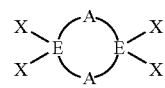

(I)

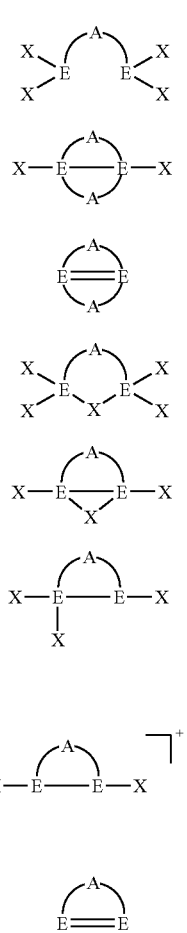

(II)
(III)
(IV)
(V)
(VI)
(VII)
(VIII)
(IX)

where
E is boron,
A is one of the following groups (X) to (XII):

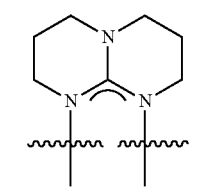

(X)

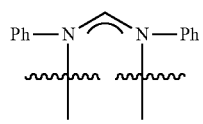

(XI)

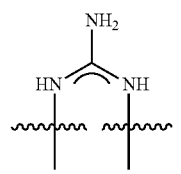

(XII)

where the (X) to (XII) radicals may be substituted by one or more straight- or branched-chain $C_{1-8}$-alkyl radicals aryl radicals and/or halogen atoms, X is selected from hydrogen, halogen, hydroxyl, thio, cyano, sulfo, carboxyl, a straight- or branched-chain $C_{1-8}$-alkyl radical, a $C_{3-7}$-cycloalkyl radical, a straight- or branched-chain $C_{2-8}$-alkenyl radical, an aryl radical, a heterocyclic radical, an arylcarbonyl radical, a $C_{1-8}$-alkylcarbonyl radical, a carbonyloxy radical, a sulfonyl radical, an amino radical, a $C_{1-8}$-alkylamino radical, a $C_{1-8}$-dialkylamino radical, an amido radical, a $C_{1-8}$-alkylamido radical, a $C_{1-8}$-dialkylamido radical, a $C_{1-8}$-alkyloxycarbonylamino radical, an aryloxycarbonylamino radical, an amidinoradical, a guanidino radical, a $C_{1-8}$-alkyloxy radical, an aryloxy radical, an arylalkyloxy radical, a sulfonylamido radical, a $C_{1-8}$-alkylsulfonylamido radical, an arylsulfonyl-amido radical, an amino acid radical or a protected acid radical, where the molecule may have two or more of the structural features shown in the formulae (I) to (IX), with the proviso that the compounds (I) to (IX) are capable either of absorbing and/or releasing hydrogen.

7. The material as claimed in claim 6, which comprises at least one compound of the following formulae (XIII) to (XV):

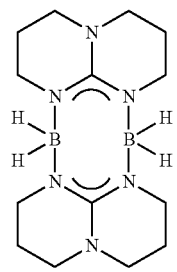

(XIII)

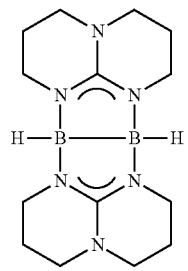

(XIV)

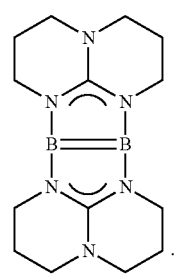

(XV)

8. A material, for reversible hydrogen storage which comprises at least one compound of the following formula (XVI):

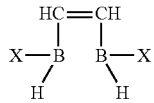

(XVI)

wherein X is as defined in claim 6.

9. A material for reversible hydrogen storage, which comprises at least one compound of the following formula (XVII):

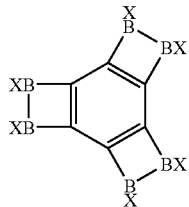

(XVII)

where X is halogen, or hydrogen.

10. A material, for reversible hydrogen storage, which comprises at least one compound of the following formula (XVIII):

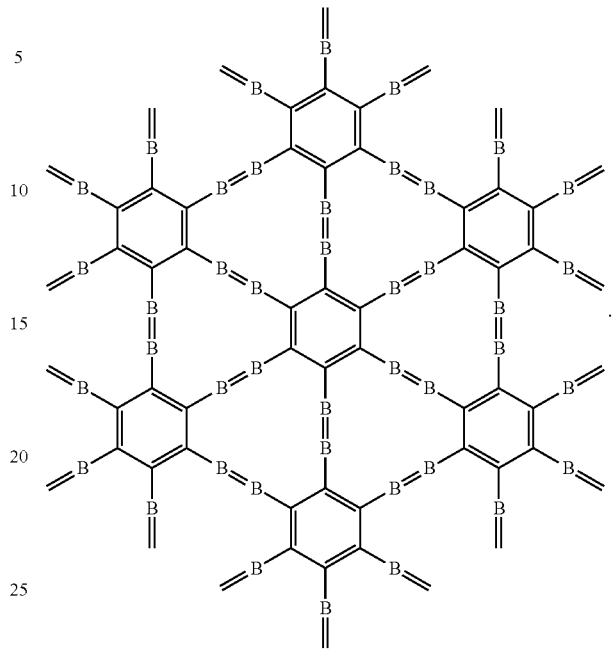

(XVIII)

11. A process for reversible hydrogen storage, wherein the process for reversible hydrogen storage comprises reacting at least one compound of the general formula (III), (IV), (VI), (VII), (VIII) or (IX) as defined in claim 1, with molecular hydrogen in order to reversibly store it, and/or heating it to a temperature in the range from 50° C. to 150° C. and/or placing a material which has reversibly stored hydrogen, comprising at least one compound of the general formula (I), (II), (III), (V), (VI), (VII) or (VIII) as defined in claim 1, under vacuum in order to release molecular hydrogen.

* * * * *